United States Patent [19]

James et al.

[11] Patent Number: 5,267,947
[45] Date of Patent: Dec. 7, 1993

[54] CONTOUR LUMBAR SUPPORT

[76] Inventors: Gene James; Kim Y. James, both of 13018 N. Joan D'Arc, Phoenix, Ariz. 85032

[21] Appl. No.: 803,038

[22] Filed: Dec. 6, 1991

[51] Int. Cl.⁵ ............................................. A61F 5/02
[52] U.S. Cl. ...................................... 602/19; 482/106; 2/311
[58] Field of Search ................. 128/78, 112.1, 117.1; 602/6, 13, 19; 482/106, 139; 2/44, 311

[56] References Cited

U.S. PATENT DOCUMENTS

| | | |
|---|---|---|
| 2,733,712 | 2/1956 | Wuesthoff ............................... 602/19 |
| 4,135,503 | 1/1979 | Romano .................................. 602/19 |
| 4,178,922 | 12/1979 | Curlee .................................... 602/19 |
| 4,178,923 | 12/1979 | Curlee .................................... 602/19 |
| 4,597,386 | 7/1986 | Goldstein . |
| 4,682,587 | 7/1987 | Curlee .................................... 602/13 |
| 4,703,750 | 11/1987 | Sebastian et al. . |
| 4,745,911 | 5/1988 | Bender . |
| 4,794,916 | 1/1989 | Porterfield et al. . |
| 4,836,194 | 6/1989 | Sebastian et al. . |
| 4,905,993 | 6/1990 | Barone .................................. 602/19 |

OTHER PUBLICATIONS

*Ironman* magazine, Jun. 1991 issue, p. 125-advertisement.
*Flex* magazine, Jul. 1991 issue-advertisement.
*Flex* magazine, illustrates belt sold under "Valeo" mark.

*Primary Examiner*—Richard J. Apley
*Assistant Examiner*—Jeanne M. Mollo
*Attorney, Agent, or Firm*—Cahill, Sutton & Thomas

[57] ABSTRACT

A belt for supporting the lumbar region of the spine provides transverse and axial support to the hard tissues, including the vertebrae and discs of the lumbar spine, while accommodating extension and contraction of the soft tissues, including the paraspinal musculatures. A compressible support extending from and fixably positioned by the belt includes a vertically transversely oriented ridge bearing against the hard tissues and interleaved troughs for nestingly receiving the soft tissues and without appreciable laterally compressive restrictive effect.

23 Claims, 2 Drawing Sheets

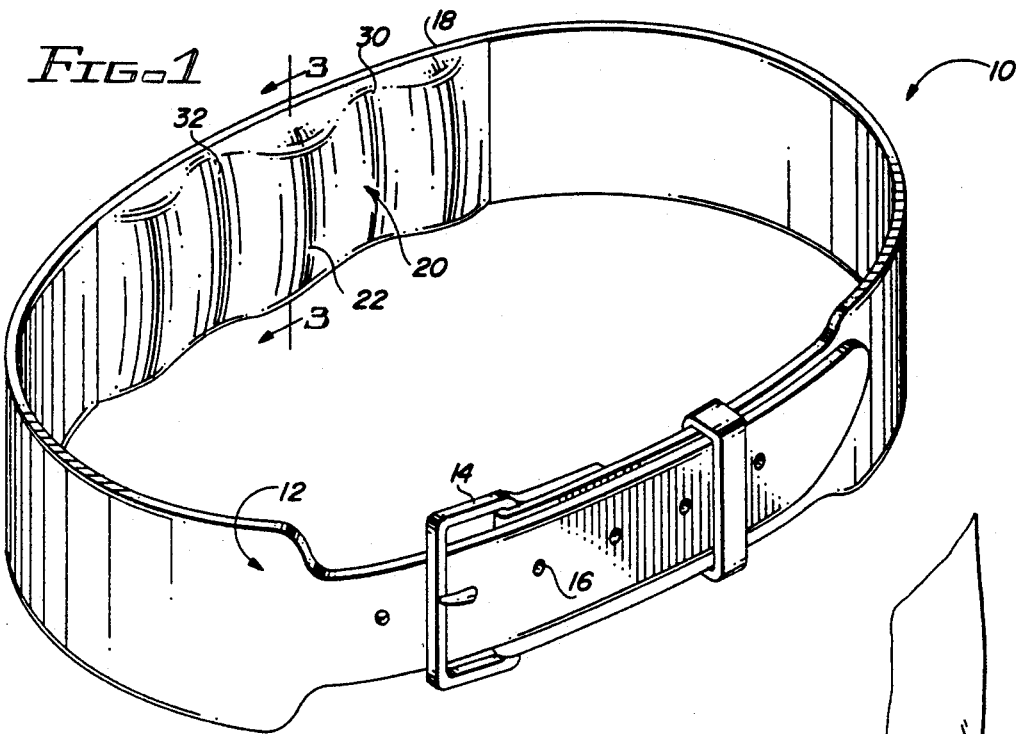
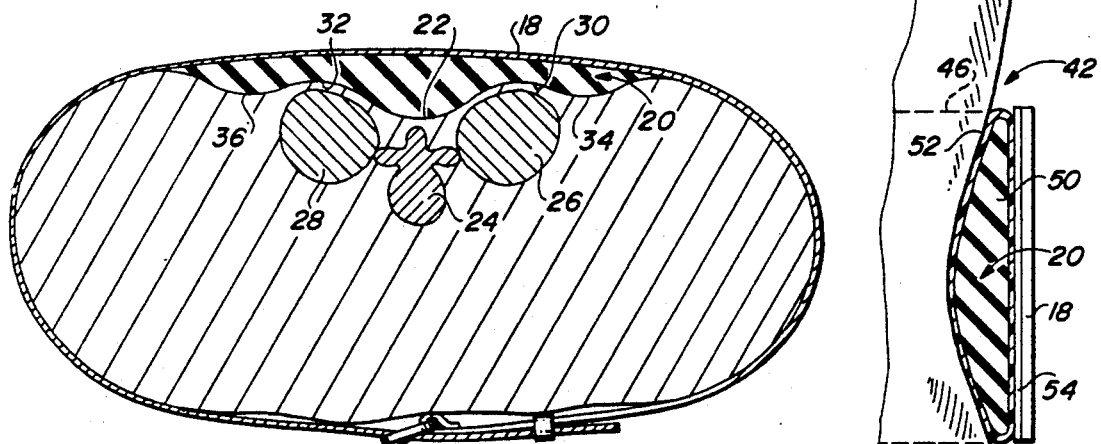
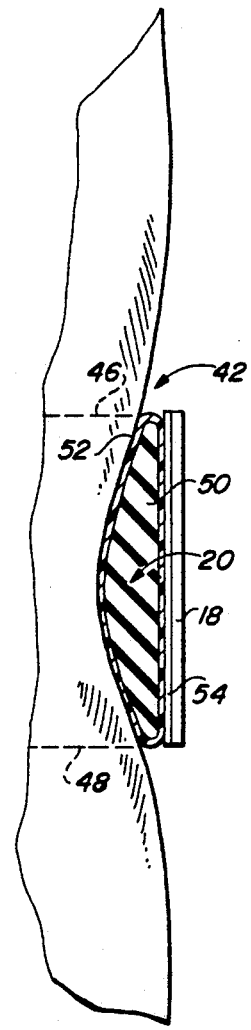
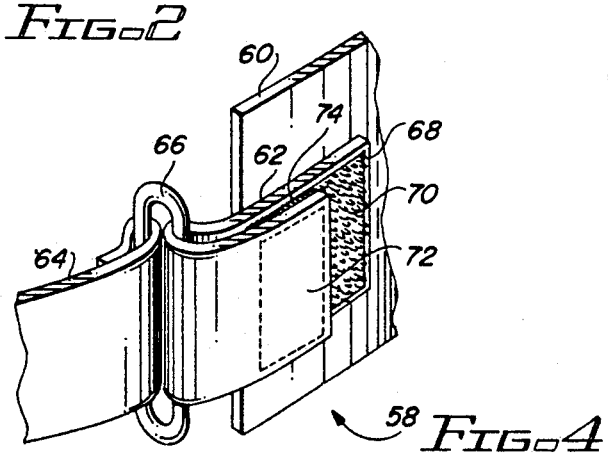

CONTOUR LUMBAR SUPPORT

BACKGROUND OF THE INVENTION

1. Field of the Invention

The present invention relates to supports for the lumbar spine and, more particularly, to a support for the adjacent hard tissues without compressing the paraspinal musculature.

2. Description of Related Prior Art

To prevent injury to the soft and hard tissues attendant the lumbar spine, belts retained about a person's midriff have been used for centuries. Similarly, such belts have been used for the purpose of restricting movement to prevent exacerbating an existing injury or damage to the hard and/or soft tissues. These belts generally serve in the manner of an encircling constrictive band that indiscriminately restricts movement of all adjacent and associated hard and soft tissues. Certain of these devices include cushions for accommodating the inward bowing of the lumbar spine; these cushions may vary in size as a function of the degree of inflation or fixed in size and density. To focus support in the lumbar region, a plurality of separate cushioning elements, of various configurations, may be positionally maintained by a supporting belt. Specific body movements such as bending, stooping, twisting, lifting, prolonged standing or sitting, etc. may place considerable strain on the lumbar spine, discs, and supporting muscles and ligaments. To a greater or lesser extent, known supports or belts to be mounted about a person's midriff do reduce the risk of injury or reduce the likelihood of exacerbating an existing injury. However, because they generally provide only transverse support to the lumbar spine, axial stability is not adequately provided.

It is well documented that most injuries to the lower back occur while a person is in flexion and rotation postures. The known belt type devices do not provide adequate protection or restraint against excessive movement of the lumbar spine during flexion and rotation. The lack of limiting the flexion and rotation postures increases the risk of injury while providing a false sense of security.

SUMMARY OF THE INVENTION

A lumbar pad, supported upon the interior surface of a midriff worn belt, includes a central axially oriented ridge for bearing against and supporting the lumbar spine. A pair of opposed adjacent troughs receive and accommodate contraction and expansion of the paraspinal musculatures without imposing significant laterally oriented pressures restrictive of muscular movement. The support pad may be contoured and reduced in thickness upwardly and downwardly from a central horizontal section to conform with the vertical lumbar curvature. Alternatively, the part of the support pad above the central horizontal section may be abruptly terminated. A variably tightenable belt provides control over the degree of pressure exerted by the support pad and the commensurate spinal support achieved.

It is therefore a primary object of the present invention to provide a contour lumbar support which supports the hard tissues without compressively restricting movement of the spinal musculature.

Another object of the present invention is to provide a support positionable and maintainable adjacent the lumbar spine which includes a ridge aligned with the general axis of the spine and interleaved channels for receiving the paraspinal musculatures.

Still another object of the present invention is to provide a support for encircling the midriff of a user without significantly restricting movement of the muscles, ligaments and tendons attendant the lumbar spine.

Yet another object of the present invention is to provide transverse and axial support to the lumbar spine.

A further object of the present invention is to provide support to the lumbar spine which support limits the extent of flexion and rotation postures of the user.

A still further object of the present invention is to provide an infinitely adjustable belt mounted contour lumbar support.

A yet further object of the present invention is to provide a method for restricting the flexion and rotation postures during exercise.

A yet further object of the present invention is to provide a method for supporting the lumbar spine without compressively restricting the paraspinal musculatures.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is an isometric view of the invention;

FIG. 2 is a partial cross-sectional view showing the invention in relation to the spine and paraspinal musculatures of a user;

FIG. 3 illustrates a side view of the contour lumbar support taken along lines 3—3, as shown in FIG. 1, and depicted adjacent the back of a user;

FIG. 4 is a partial illustration of an adjustable belt fitting;

DESCRIPTION OF THE PREFERRED EMBODIMENT

Figure 5:
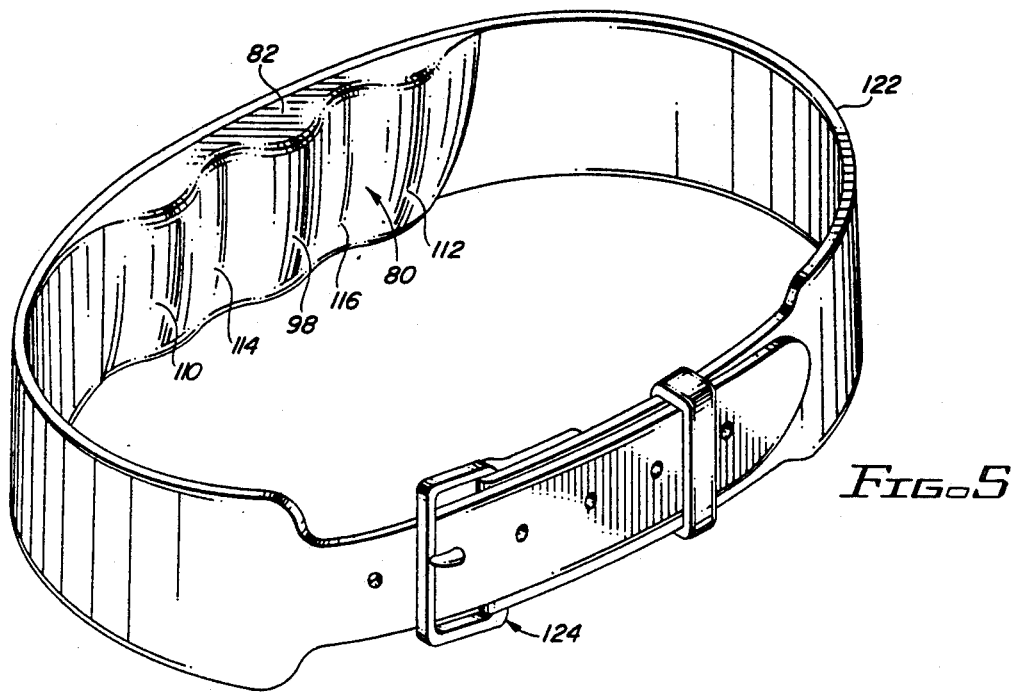
FIG. 5 is an isometric view of a variant of the invention.

Contour lumbar support 10 illustrated in the drawings was developed to minimize the stress on the lumbar spine by providing axial as well as transverse support to the lumbar spine. The contour lumbar support is maintained in place to provide the requisite support through a belt 12. The belt may include a conventional buckle 14 engaging one of holes 16; alternatively, an infinitely adjustable strap may be used, as illustrated in FIG. 4.

Support pad 20 extends radially inwardly from rear section 18 of belt 12 for engaging the lumbar region of a user. The support pad includes a generally axially (vertically) aligned ridge 22. As particularly illustrated in FIG. 2, ridge 22 is oriented and located to bear against and provide support to the elements of lumbar spine 24. Immediately adjacent and on opposed sides of the lumbar spine are lumbar paraspinal musculatures 26,28, which extend axially (generally vertically). Troughs 30,32 of support pad 20 receivingly accommodate these musculatures without laterally oriented compression and accommodate longitudinally (vertically) oriented expansion and compression. The troughs, extend partially about each grouping of musculatures, as illustrated. The support for each grouping of musculatures is further provided by the surfaces of the troughs extending from the base of troughs 30,32 to adjacent ridges 22,34 and 22,36, respectively.

Upon substantial tightening of belt 12, a great deal of support can be provided to lumbar spine 24 by ridge 22 of the support pad bearing thereagainst. Such great support will tend to stabilize and maintain the lumbar spine to a degree sufficient to resist injurious movement during both modest and severe or strenuous exercise, including flexion and rotation postures. Simultaneously, the accommodating depressions provided by troughs 30 and 32 will prevent the pressures associated with a substantially tightened belt from compressing laterally and otherwise impeding normal axial (vertical) musculature movement of the lumbar paraspinal musculatures. The lack of reduction in effectiveness of the paraspinal musculatures due to the configuration of support pad 20 permit the paraspinal musculatures to act in the normal manner during flexion and rotation postures. The resulting lack of constraint will tend to reduce the likelihood of injuries occurring when the person is exercising and posturing. Furthermore, the reduced or even lack of constraint upon the paraspinal musculatures will provide increased strength. The greater freedom of movement will enhance endurance in combination with increased strength.

As illustrated in particular in FIG. 3, support pad 20 is tapered (reduced in thickness) upwardly and downwardly from a mid-vertical portion to accommodate the normal curvature of a user's back 42. The ridges and troughs of support pad 20 (see FIGS. 1 and 2), have a commensurate taper with respect to rear section 18 of supporting belt 12 as a function of the distance from the respective top and bottom edges 46,48 of the belt. Moreover, support pad 20 may be formed by a pad 50 enclosed within a fixed or removable sheath 52. If the sheath is removable from about the support pad and detachably attached to belt 12, it may be cleaned periodically. Such detachable attachment may be by use of conventional hook and loop attachment means 54 disposed intermediate support pad 20 and belt 12.

While a conventional belt buckle and strap arrangement, as illustrated in FIGS. 1 and 2, may be adequate in most applications, finer control over the amount of support provided by support pad 20 can be achieved by use of an infinitely adjustable belt. A belt fastener 58 for this purpose is illustrated in FIG. 4. Herein belt end 60 includes a strap 62 extending therefrom. Belt end 64 may include an oval ring 66 for penetrable engagement by strap 62. Base 68 of strap 62 may include a pad 70 of loop material of the type used in conventional hook and loop attachment means. End 72 of the strap may include a pad 74 of hook material for engagement with the pad of loop material. Thereby, end 72 of strap 66 after penetrable engagement with oval ring 66 may be drawn toward belt end 60 to a greater or lesser degree, depending upon the degree of tightness of the belt desired and thereafter maintained in place by engaging the opposed pads of hook and loop attachment means.

Figure 6:
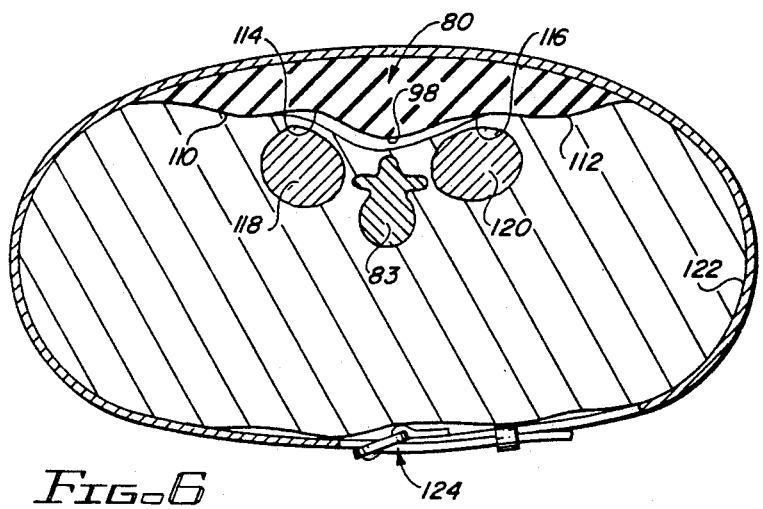
FIG. 6 is a partial cross-section view of the variant and showing the invention in relation to the spine and paraspinal musculatures of a user.
Figure 7:
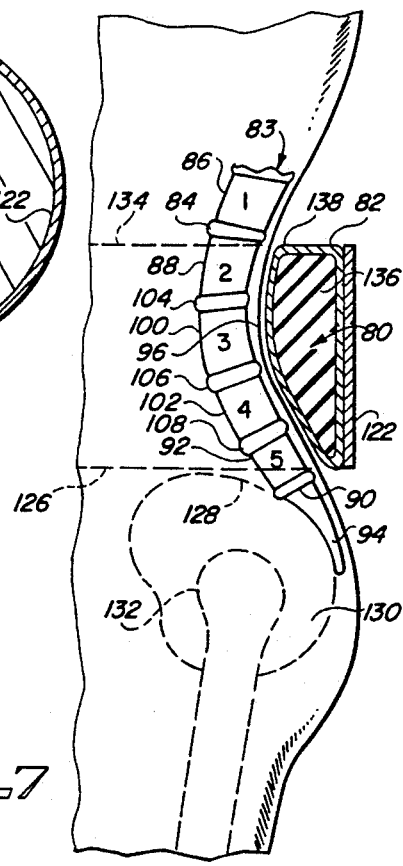
FIG. 7 illustrates a cross-sectional side view of the contour lumbar support shown in FIGS. 5 and 6 and depicted adjacent the back of a user.

The variant contour lumbar support 80 illustrated in FIGS. 5, 6 and 7 was developed to eliminate resistance acting against the spine 83 during a back bend. For this reason, it includes a shelf-like top surface 82. Correct positioning of the variant contour lumbar support will locate this top surface essentially adjacent intervertebral disk 84 disposed intermediate the first and second lumbar vertebrae 86,88. The lower end of the variant contour lumbar support is located proximate intervertebral disk 90 disposed intermediate the fifth lumbar vertebrae 92 and the sacrum 94. Anterior surface 96, generally coincident with ridge 98, bears against the second, third, fourth and fifth lumbar vertebrae, 88, 100, 102 and 92 and the interleaving intervertebral disks 104, 106 and 108.

Variant contour lumbar support 80 includes three ridges, ridge 98 flanked by ridges 110 and 112 similar to that of contour lumbar support 20. Similarly, troughs 114 and 116 are disposed intermediate the respective ridges to receive and accommodate the paraspinal musculatures 118,120, as depicted in FIG. 6.

Belt 122 secures variant contour lumbar support 80 in place. It is secured by a buckle 124, as illustrate or by the variant attachment device illustrated in FIG. 4 or other attachment means. For proper location of the variant contour lumbar support, lower edge 126 of the belt should be essentially coincident with iliac crest 128 of the ilium 130. For illustrative and orientational purposes, hip joint 132 is also illustrated. Upper edge 134 of the belt is generally coincident with the upper edge of the second lumbar vertebrae 88 and intervertebral disk 84, as illustrated.

Variant contour lumbar support 80 may be formed of a pad 136 of resilient material. For structural purposes, as well as for reasons of cleanliness, the pad may be removably or permanently enclosed within a sheath 138.

The effectiveness of the pads is a function the degree of support provided to the lumbar spine and the degree of accommodation provided to the lumbar paraspinal musculatures. Since the latter, in particular, will change in size and configuration as a function of an intensive exercise program, differently sized support pads may be necessary to provide the most support possible and thereby enhance injury free exercise activities. Thus, the pads may be replaceable to accommodate growth or change in the surface contours of the lumbar region of the user as a function of musculature development and strength acquired during an exercise program. Such replacement may be effected by detachably attaching the pads to the belt.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. Apparatus for supporting the lumbar spine and lumbar paraspinal musculatures of a user, said apparatus comprising in combination:
   a) a belt for engaging the midriff of a user; and
   b) a support pad retained in place against the lumbar spine by said belt for supporting the lumbar spine while accommodating normal axial movement of the lumbar paraspinal musculature, said support pad having a longitudinal axis generally aligned with said belt and a lateral axis,
   said support pad including a first ridge oriented parallel with the lateral axis for bearing against and supporting the lumbar spine, a second ridge oriented generally parallel with said first ridge and displaced along the longitudinal axis of said support pad on one side of said first ridge, a third ridge oriented generally parallel with said first ridge and displaced along the longitudinal axis of said support pad on the other side of said first ridge, a first trough disposed on one side of said first ridge between said first ridge and said second ridge for receiving the paraspinal musculatures disposed on the corresponding side of the spine and a second trough disposed on the other side of said first ridge between said first ridge and said third ridge for receiving the paraspinal musculatures disposed on the corresponding side of the spine.

2. The apparatus as set forth in claim 1 wherein said support pad includes upper and lower edges and wherein the thickness of said support pad is tapered vertically from a central horizontal portion toward each of the upper and lower edges.

3. The apparatus as set forth in claim 1 wherein said support pad includes a protective sheath.

4. The apparatus as set forth in claim 1 including means for detachably attaching said support pad with said belt.

5. The apparatus as set forth in claim 1 wherein said support pad tapers in thickness laterally in at least one direction.

6. The apparatus as set forth in claim 1 wherein the thickness of said support pad tapers laterally in each direction from a longitudinal portion.

7. The apparatus as set forth in claim 6 including means for detachably attaching said support pad with said belt.

8. The apparatus as set forth in claim 1 including means for adjusting the tightness of said belt about the midriff of the user.

9. The apparatus as set forth in claim 1 wherein said support pad includes an upper edge, said upper edge being truncated and defining a flat surface extending essentially horizontally from the back of a user upon engagement of said belt about the midriff of the user.

10. The apparatus as set forth in claim 1 wherein said support pad includes a lower edge defined by a downwardly tapered lower part of said support pad and a substantially planar surface defining the upper extremity of an upper part of said support pad.

11. The apparatus as set forth in claim 1 wherein said support pad includes a rear surface and an upper surface, said upper surface extending from said rear surface into intersecting relationship with said first, second and third ridges and said first and second troughs.

12. Apparatus for protecting the lumbar spine of a user without compressing the paraspinal musculatures, said apparatus comprising in combination:
 a) means for exerting pressure against the lumbar spine to support the lumbar spine and for exerting pressure laterally adjacent one side of each of the paraspinal musculatures;
 b) means for accommodating unrestricted normal axial movement of the paraspinal musculatures disposed on opposed sides of the spine;
 c) further means for exerting pressure on the lumbar region of a user laterally immediately adjacent and extending along the other side of each of the paraspinal musculatures;
 d) means for retaining said exerting means, said accommodating means and said further exerting means adjacent to and defining continuous contact with the lumbar region of a user.

13. The apparatus as set forth in claim 12 wherein said exerting means comprises a ridge and said accomodating means comprises a trough disposed on each side of said ridge.

14. The apparatus as set forth in claim 12 wherein said retaining means includes means for adjusting the degree of support provided by said exerting means.

15. The apparatus as set forth in claim 12 including means for adjusting said retaining means to alter the force of said exerting means bearing against the lumbar spine.

16. The apparatus as set forth in claim 12 wherein said accommodating means includes means for partially encircling each of the paraspinal musculatures.

17. Apparatus for protecting the lumbar spine of a user without compressing the paraspinal musculature, said apparatus comprising in combination:
 a) means for exerting pressure against the lumbar spine to support the lumbar spine;
 b) means for accommodating unrestricted normal axial movement of the paraspinal musculatures disposed on opposed sides of the spine, said accommodating means including means for partially encircling each of the paraspinal musculatures;
 c) further means for exerting pressure on the lumbar region of a user laterally adjacent each of the paraspinal musculatures on a side opposed to the spine, said further exerting means includes a first ridge displaced from said exerting means for defining a first trough of said accommodating means and disposed intermediate said first ridge and said exerting means and a second ridge displaced from said exerting means for defining a second trough of said accommodating means and disposed intermediate said second ridge and said exerting means;
 d) means for retaining said exerting means, said accommodating means and said further exerting means adjacent the lumbar region of a user.

18. The apparatus as set forth in claim 17 wherein said exerting means, said first and second ridges and said first and second troughs collectively include portions tapering vertically downwardly.

19. A method for protecting the lumbar spine and the paraspinal musculature of a user during exercise, said method comprising the steps of:
 a) supporting the lumbar region of the user with a support pad;
 b) urging a first ridge of the support pad against the lumbar spine to support the lumbar spine;
 c) accommodating normal axial movement during exercise of the paraspinal musculatures disposed on opposed sides of the lumbar spine with corresponding troughs formed in the support pad on opposed sides of the first ridge;
 d) further urging a second ridge of the support pad against the lumbar region laterally of the paraspinal musculatures on one side of the lumbar spine to support the lumbar region;
 e) yet further urging a third ridge of the support pad against the lumbar region laterally of the paraspinal musculatures on the other side of the paraspinal musculatures of the lumbar spine to support the lumbar region; and
 f) retaining the support pad adjacent the lumbar region.

20. A method as set forth in claim 19 wherein said step of accomodating includes the step of partially encircling the respective paraspinal musculature.

21. A method as set forth in claim 19 wherein said step of urging includes the step of providing support to the second, third, fourth and fifth lumbar vertebrae.

22. A method as set forth in claim 19 wherein said step of retaining includes the step of locating the support pad adjacent the second, third, fourth and fifth lumbar vertebrae with a belt.

23. A method as set forth in claim 21 wherein said step of retaining includes the step of positioning the belt to locate the support pad at and above the iliac crest.

* * * * *